United States Patent [19]

Powers et al.

[11] 4,238,490

[45] Dec. 9, 1980

[54] ANTIHYPERTENSIVE PYRIDAZIN(2H)-3-ONES

[75] Inventors: Larry J. Powers, Madison; Zaven S. Ariyan, Mentor; Russell Buchman, Madison; James A. Scozzie, Painesville; Robert E. Moser, Mentor; William J. Pyne, Painesville, all of Ohio

[73] Assignee: Diamond Shamrock Corporation, Dallas, Tex.

[21] Appl. No.: 11,416

[22] Filed: Feb. 12, 1979

[51] Int. Cl.³ .................. A01N 31/50; C07D 237/14; C07D 237/24; C07D 237/22
[52] U.S. Cl. ..................................... 424/250; 544/114; 544/238; 544/239; 544/240; 260/154; 424/248.5; 424/248.52; 424/248.54; 424/180; 536/55
[58] Field of Search ............... 544/239, 240, 238, 114; 260/154; 424/250, 248.5, 248.52, 248.54, 180; 536/55

[56] References Cited
U.S. PATENT DOCUMENTS 3,900,483  8/1975  Fujimatsu et al. .................. 544/239

OTHER PUBLICATIONS

Wagner et al., Chem. Abs., 79, 19021k, (1973).
Nannini et al., Europ. J. Med. Chem., 14, 53–60, (1979).
Schmidt et al., Helv. Chem. Acta., 40, 1749–1756, (1957).

*Primary Examiner*—Mark L. Berch
*Attorney, Agent, or Firm*—Stuart L. Melton

[57] ABSTRACT

Compounds of the formula

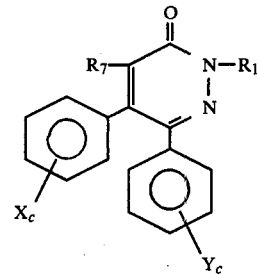

are useful antihypertensive agents.

18 Claims, No Drawings

ANTIHYPERTENSIVE PYRIDAZIN(2H)-3-ONES

BACKGROUND OF THE INVENTION

The present invention relates generally to pharmacologically active pyridazinones and, more particularly, to certain novel antihypertensively effective substituted pyridazin(2H)-3-one compounds.

Substituted pyridazinone compounds having various substituents thereon have heretofore been prepared and proposed for use in a wide range of different ultimate applications.

For example, U.S. Pat. No. 3,689,652 discloses 6-(substituted phenyl)-4,5-dihydro-3(2H)-pyridazinones as hypotensive agents. More specifically, 6-halomethylphenyl-5-methyl (or unsubstituted)-4,5-dihydro-3(2H)-pyridazinone compounds are disclosed. In related U.S. Pat. Nos. 3,746,712, 3,812,256, 3,822,260, 3,876,786 and 3,876,787, the patentees further disclose corresponding 6-substituted phenyl-4,5-dihydro-pyridazinone compounds wherein the additional phenyl substituents include lower alkanoyl, nitro, amino, lower alkanoylamino and cyano wherein the 2- position of the pyridazinone ring may be optionally substituted by lower alkyl.

U.S. Pat. No. 3,657,242 discloses a series of 4,5-dihydro-pyridazin(2H)-3-one and hexahydropyridazines and, more specifically, certain 2-hydroxyalkyl-6-aryl or heterocyclic substituted-4,5-dihydro-pyridazinones and hexahydropyridazines useful as antiinflammatories.

In U.S. Pat. No. 3,931,177, the patentees disclose a series of 6-(3-substituted amino-2-hydroxy propoxyaryl)-4,5-dihydro-3(2H)-pyridazinones active as β-adrenergic-blocking agents and antihypertensives.

The patentees in U.S. Pat. No. 3,975,388 disclose 6-alkoxy-, alkyl-, hydroxymethyl-, cycloalkylamino-, alkylamino- and heterocyclic-substituted phenyl-4,5-dihydro-3(2H)-pyridazinone compounds having antihypertensive activity.

The foregoing compounds are representative of 4,5-dihydro-pyridazinone compounds previously suggested as pharmacologically active compounds. As a chemical class, the foregoing compounds comprise dihydro (saturated) ketopyridazines.

Representative of another class of related compounds are the pyridaz-3-one compounds disclosed in U.S. Pat. No. 2,839,532. The aforesaid patent is directed to 4,5-unsaturated pyridaz-3-one (or 3-ketopyridazine) compounds having a cyano, acetyl, carboxyl, carboethoxy or benzoyl group in the 4- position optionally substituted in 5,6-positions by lower alkyl, phenyl or substituted phenyl residues. These compounds are disclosed as being useful as medicaments, particularly, analgesics, anesthetics, antibacterials or disinfectants.

U.S. Pat. No. 3,491,096 and British Pat. No. 840,522 are directed to other previously investigated pyridazone compounds. The aforementioned British patent pertains to 2-hydroxymethyl-6-phenyl-3-pyridazone and the analgesic utility thereof. U.S. Pat. No. 3,491,096 describes 2-pyridylalkylated-6-phenyl-pyridaz-3-one compounds possessing sedative, analgesic and antispasmodic properties, with occasional hypotensive effects being observed.

SUMMARY OF THE INVENTION

It is, therefore, a primary object of the present invention to afford novel substituted pyridazin(2H)-3-one compounds, which possess antihypertensive activity.

It is a further object of the present invention to provide methods for obtaining antihypertensive effects in mammals by the administration of preselected dosages of active substituted pyridazinone compounds or pharmaceutically acceptable salts thereof in appropriate nontoxic pharmaceutical dosage unit forms or compositions.

A still further object of the present invention is to provide dosage unit forms adapted for, e.g., oral, rectal, parenteral, etc., administration and useful in the treatment, management and mitigation of hypertensive conditions or disorders.

These and other similar objects, advantages and features are accomplished according to the products, compositions and methods of the invention comprised of novel substituted pyridazinones, compositions derived therefrom and antihypertensive methods employing same.

DESCRIPTION OF THE PREFERRED EMBODIMENTS

It has now been found, in accordance with the present invention, that pyridazin(2H)-3-ones of the general formula

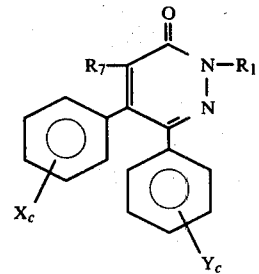

or a pharmaceutically acceptable nontoxic salt thereof wherein $R_1$ is hydrogen, $C_1$–$C_4$ hydroxyalkyl, $C_1$–$C_4$ carbamylmethyl, $C_1$–$C_6$ carboxyalkyl, $C_1$–$C_6$ alkoxycarbonyl($C_1$–$C_6$)alkyl, $C_1$–$C_6$alkoxy($C_1$–$C_6$)alkyl; or the group

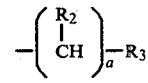

where a is 1 to 4, inclusive, $R_2$ is hydrogen or $C_1$–$C_4$ alkyl and $R_3$ is amino, methylthio, $C_1$–$C_6$ alkylamino, $C_1$–$C_6$ alkylimino, $C_1$–$C_6$ acylamino, $C_1$–$C_6$ alkoxycarbonyl amino, morpholinyl, piperizinyl, ($C_1$–$C_6$ alkoxycarbonyl)piperizinyl, piperidinyl, pyrrolidinyl, glucuronyl or glucopyranosyl; or the group

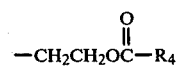

where $R_4$ is hydrogen, $C_1$-$C_{20}$ alkyl, $C_1$-$C_6$ carboxyalkyl, phenyl, phenyl($C_1$-$C_6$)alkyl or $R_4$ represents the group

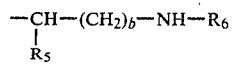

where b is 0 to 4, inclusive, $R_5$ is hydrogen, $C_1$-$C_4$ alkyl, methylthioethyl, benzyl, $NH_2$, or benzyloxycarbamyl, and $R_6$ is hydrogen, benzyloxycarbonyl, t-butyloxycarbonyl or

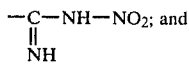

$R_7$ is acetyl, cyano, phenylsulfonyl, ($C_1$-$C_4$)alkylhydrazono, naphthyl, phenyl or phenyl substituted with at least one substituent selected from the group consisting of halogen, $C_1$-$C_6$ alkylamino and $C_1$-$C_4$ alkoxy; and $X_c$ and $Y_c$ are the same or different and independently selected from the group consisting of halogen, $C_1$-$C_4$ alkyl and $C_1$-$C_4$ alkoxy where c is 0, 1 or 2; subject to the provisos that when $R_7$ is acetyl, phenyl or cyano, $R_1$ is other than hydrogen; and when $R_7$ is cyano, $R_1$ is $C_1$-$C_4$ hydroxyalkyl, $C_1$-$C_6$ carboxyalkyl or the group

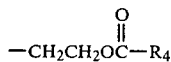

where $R_4$ is $C_1$-$C_6$ carboxyalkyl and $X_c$ and $Y_c$ are halo, with c being at least 1;
and the enol tautomeric derivatives and metabolites thereof are useful therapeutic antihypertensive agents.

As used throughout the instant specification and claims, the expressions "alkyl" and "alkoxy" are inclusive of straight and branched chain carbon-carbon linkages, e.g., methyl, ethyl, n-propyl, isopropyl, n-butyl, isobutyl, sec-butyl, tert-butyl, isohexyl, etc. The expression "acyl" includes, e.g., formyl, acetyl, propionyl, butanoyl, pentanoyl, hexanoyl and the like. The term "halo" includes chlorine, fluorine, bromine and iodine. The expression "pharmaceutically acceptable nontoxic salts," as used herein, is intended to include those salts capable of being formed with the instant compounds and substituted derivatives thereof in accordance with the invention without materially altering the chemical structure or pharmacological properties of the parent compounds. Representative of acids for reaction with sufficiently basic pyridazinone derivatives include hydrochloric, hydrobromic, hydroiodic, nitric, phosphoric, citric, etc. Alkali metal salts of carboxylic acid derivatives of the invention may be obtained by reaction with suitable bases, e.g., sodium hydroxide, potassium hydroxide, etc. Alkaline earth metal salts may be similarly obtained. Additionally, the compounds of the invention containing amino acid residues, i.e., an α-amino acyl group, may be obtained as their hydrate salts such as mono- or di-hydrobromide, hydrochloride, etc., hydrate and such inorganic and organic acid addition salts of certain of the compounds of the present invention and amino acid residues or derivatives may advantageously be employed to, for instance, alter solubility properties or augment bioavailability.

As will be apparent to those skilled in the art, the keto compounds of the above formula wherein $R_1$ is hydrogen may be present in the enol tautomeric form. It is also noted that certain of the $R_1$ substituents at the 2-position, e.g., hydroxyalkyl, carboxyalkyl, alkoxycarbonylalkyl, alkoxyalkyl, alkylaminoalkyl, glucuronyl, etc., constitute possible enolic derivatives and/or metabolites of compounds within the scope of the present invention.

The pyridazinone, i.e., substituted keto-pyridazine compounds of the present invention, may be prepared by various alternative methods heretofore employed in the synthesis of other pyridazinone compounds or modifications thereof to obtain the $R_1$, $R_7$, $X_c$ or $Y_c$ substituents thereon as defined above. In general, one method for the preparation of pyridazin(2H)-3-ones comprises reacting an appropriately substituted monohydrazone, with the appropriately substituted acetic acid ester or reacting the appropriately substituted benzil and appropriately substituted hydrazide under cyclization conditions, e.g., in the presence of suitable solvents, such as xylene, acetonitrile, methanol, benzene, etc., and alkaline condensing agents, such as hydroxides, alcoholates, hydrides, alkali or alkaline earth metals, tertiary amines, etc., to effect ring closure. The foregoing general reaction scheme may be depicted as follows

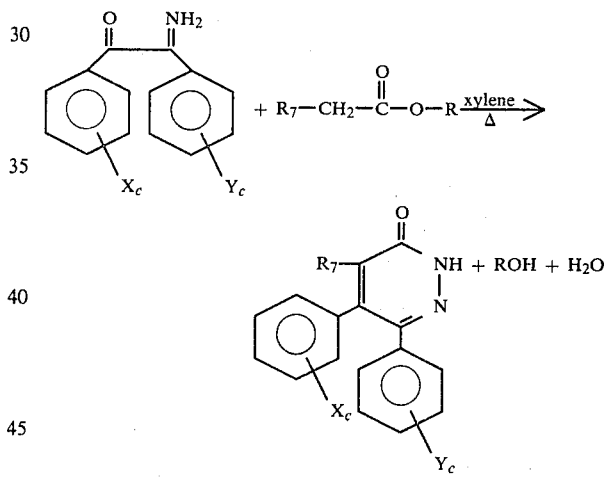

The monohydrazone reactants may be prepared by the reaction of an appropriate substituted benzil with hydrazine hydrate. Suitable benzyl starting materials may be obtained commercially or prepared by known methods, for example, cyanide ion catalyzed benzoin condensation followed by oxidation. The pyridazin(2H)-3-one compounds thus prepared may be utilized following suitable recrystallization/purification as an intermediate for the preparation of further 2-substituted derivatives in accordance with the above $R_1$ definition as illustrated more particularly in the specific examples of preferred embodiments of the invention hereinafter.

As previously indicated, the compounds of the present invention evidence antihypertensive effects in warm-blooded animals. Of course, it will be appreciated that the specific response elicited upon administration of the compounds of the present invention to an animal species in need thereof will vary depending upon the specific structure of the administered compound, the unit dose, dosage regimen and mode of administration, as well as the mammalian species involved.

Exemplary of preferred compounds for use in the antihypertensive compositions and methods of the present invention are compounds of the above general formula wherein, correspondingly, $R_1$ represents $C_1$-$C_4$ hydroxyalkyl (especially, hydroxyethyl), esters thereof, e.g., acetate, butyrate, propanoate, formate, hemisuccinate, octadecanoate, benzoate, etc.; amino acid esters thereof corresponding to the

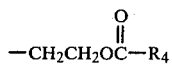

group defined hereinabove wherein $R_4$ represents

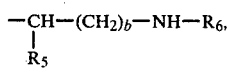

e.g., lysine, glycine, methionine, phenylalanine, etc.; or where $R_1$ is $C_1$-$C_4$ carbamylmethyl, e.g., α-acetamide; aminoalkyl, e.g., aminomethyl, aminoethyl, etc.; $C_1$-$C_6$ alkylaminoethyl, e.g., dimethylaminoethyl; glucopyranosyl; glucuronyl; 1-morpholinylethyl; 1-piperidinylethyl; 1-pyrrolidinylethyl and acetamidoethyl; and wherein $R_7$ represents acetyl and $X_c$ and $Y_c$ are para-halo, preferably, para-chloro.

In accordance with the practices of the present invention, the active compounds of the invention may be administered alone or in combination with each other or administered in admixture with pharmaceutical diluents, carriers, excipients or adjuvants suitably selected with respect to the intended route of administration and conventional pharmaceutical practices. For instance, for oral administration in the form of tablets or capsules, the active compound or compounds of the invention may be combined with such excipients as starch, lactose, sucrose, cellulose, magnesium stearate, and the like. Similarly, injectable dosage unit forms may be utilized to accomplish intravenous, intramuscular or subcutaneous administration and, for such parenteral administration, suitable sterile aqueous or nonaqueous solutions or suspensions, optionally containing appropriate solutes to effectuate isotonicity, will be employed. Other suitable adjuvants and dosage forms will be apparent to those skilled in the art.

Compounds of the invention or compositions thereof may be administered to warm-blooded animals, i.e., mammals, including, for instance, mice, rats, guinea pigs, dogs and other domesticated animals, or humans. Dosages sufficient to elicit the above-indicated antihypertensive response will generally range between about 1 to 300 mg/kg/day in laboratory mice based upon body weight, and, preferably, between about 10 to 150 mg/kg/day. The foregoing dosages will normally be administered in three or four divided doses, depending upon the desired dosage regimen. Of course, the actual effective dosage to be administered will vary, depending upon the specific compound involved, as well as the age, weight and responsiveness of the particular animal species.

The compounds of the invention exhibit relatively low toxicities and the acute oral $LD_{50}$ (lethal dose to 50 percent of mice) will generally be greater than 300 mg/kg and, with respect to certain compounds, up to as high as 8,000 mg/kg.

The following nonlimiting examples are afforded in order that those skilled in the art may more readily understand the present invention and specific preferred embodiments thereof with respect to the preparation of starting materials, intermediates and compounds in accordance with the foregoing description.

EXAMPLE 1

4-Acetyl-5,6-Bis(p-Chlorophenyl)-2H-Pyridazin-3-One

Ethanol, dried by distilling from Mg-$I_2$, was added to a dry flask ($N_2$ atmosphere) containing clean sodium (1.1 equivalent). After the sodium had reacted, ethylacetoacetate (7 ml) was added dropwise to the cold (0°–5° C.) alkoxide solution. p,p'-Dichlorobenzil monohydrazone (15 g) was added through a powder addition funnel. After heating the reaction mixture at reflux for three hours, it was cooled and poured into 1 N HCl. The resulting precipitate was separated by filtration and washed with water. The resulting product was recrystallized from ethanol-acetonitrile to obtain the title compound (20 percent yield), m.p. 269°–271° C.

Analysis—calculated for $C_{18}H_{12}Cl_2N_2O_2$(%): C, 60.20; H, 3.34; N, 7.80. Found (%): C, 60.02; H, 3.33; N, 7.91.

EXAMPLE 2

2-(2'-Hydroxyethyl)-4-Acetyl-5,6-Bis(p-Chlorophenyl)-2H-Pyridazin-3-One

The compound of Example 1 (3.1 g), ethylene carbonate (2.0 g), and potassium hydroxide (powdered) were dissolved in dimethylformamide (50 ml) and the flask placed in an oil bath (110°–120° C.) until $CO_2$ evolution ceased (ca. 3.5 hours). The reaction mixture was poured into water (400 ml) and chilled at 5° C. for 1 hour. The resulting precipitate was separated by filtration and recrystallized from methanol (85 ml) to obtain the title compound (68 percent yield) as pale yellow crystals, m.p. 191°–193° C.

Analysis—calculated for $C_{20}H_{16}Cl_2N_2O_3$ (%): C, 59.56; H, 4.00; N, 6.95. Found (%): C, 59.44; H, 3.94; N, 6.71.

EXAMPLE 3

4-Phenyl-5,6-Bis(p-Methylphenyl)-2H-Pyridazin-3-One 4,4'-Bis-p-methylbenzilmonohydrazone (10.09 g) and 6.6 g of ethylphenylacetate were charged to a dry flask in 250 ml of absolute ethanol. With stirring, 3.0 g of sodium ethoxide were added portionwise. After addition, the reaction was heated to reflux for 5.5 hours. The hot solution was quenched in an equal volume of 1 N HCl to obtain a dispersion. Upon refrigeration, a solid was obtained, which was filtered and washed with ether. The resultant product was recrystallized from acetonitrile and dried for 5 hours to obtain the title compound (48 percent yield) as an off-white solid, m.p. 282°–284° C.

Analysis—calculated for $C_{24}H_{20}N_2O$(%): C, 81.78; H, 5.72; N, 7.95. Found (%): C, 81.40; H, 5.87; N, 8.12.

EXAMPLE 4

2-(2'-Hydroxyethyl)-4-Phenyl-5,6-Bis(p-Methylphenyl)-2H-Pyridazin-3-One

4-Phenyl-5,6-bis(p-methylphenyl)-2H-pyridazin-3-one (1.8 g) and 0.88 g of ethylene carbonate were charged to a flask in 100 ml dimethylformamide. The flask was placed in an oil bath, preheated to 150° C. and the reaction was heated for 4 hours. The hot solution was quenched in an equal volume of 1 N HCl, causing a white solid to precipitate. The cooled solution was filtered and the solid recrystallized from ethyl acetate and dried for 5 hours, m.p. 192°–194° C.

Analysis—calculated for $C_{26}H_{24}N_2O_2$(%): C, 78.6; H, 6.10; N, 7.06. Found (%): C, 78.88; H, 6.06; N, 6.95.

EXAMPLE 5

2-(2'-Hydroxyethyl)-4,5,6-Triphenyl-2H-Pyridazin-3-One

Sodium (11.5 g) was allowed to react with ethanol and then benzilmonohydrazone (120 g) and ethyl phenylacetate (84 g) were added and the reaction mixture heated at reflux for 3 hours. The reaction was quenched in water and the suspension acidified. The resulting precipitate was separated and refluxed with acetonitrile, cooled and separated by filtration to obtain 4,5,6-triphenyl-2H-pyridazin-3-one (30 percent yield), m.p. 290°–292° C.

To 4,5,6-triphenyl-2H-pyridazin-3-one (6.0 g) were added 50 ml of dimethylformamide and a solution of sodium hydroxide pellets (0.7 g) dissolved in 5 ml of water. The resultant slurry was stirred at room temperature, while adding dropwise, 1.5 g of 2-chloroethanol. The mixture was heated to 110° C. for 1 hour and then allowed to heat for 16 hours at 90° C., after which time, the dimethylformamide was removed by evacuation. The residue was redissolved in methanol from which the compound was triturated, filtered and washed with petroleum ether to obtain the title compound (25 percent yield), m.p. 189° C. (dec).

Analysis—calculated for $C_{24}H_{20}N_2O_2$(%): C, 78.24; H, 5.47; N, 7.61. Found (%): C, 78.23; H, 5.47; N, 7.37.

EXAMPLE 6

4-Cyano-5,6-Bis(p-Chlorophenyl)-2H-Pyridazin-3-One

Absolute ethanol (400 ml) and sodium metal (2.3 g) were added to a dry reaction flask. After the sodium had dissolved, 4-chlorobenzil monoacetohydrazide (29.1 g) and ethyl cyanoacetate (52.6 g) were added and heated to reflux for 3 hours. The ethanol was stripped and the solid washed with hot water (ca. 400–500 ml). The title compound was obtained as a gray solid following recrystallization from absolute ethanol (50 percent yield), m.p. 271°–272° C.

Analysis—calculated for $C_{17}H_9Cl_2N_3O$ (%): C, 59.7; H, 2.7; N, 12.3. Found (%): C, 59.7; H, 2.8; N, 12.4.

EXAMPLE 7

2-(2'-Hydroxyethyl)-4-Cyano-5,6-Bis(p-Chlorophenyl)-2H-Pyridazin-3-One

Ethylene carbonate (4.4 g), dry dimethylformamide (100 ml) and 2 pellets of potassium hydroxide were added to the compound obtained from Example 6 (16.0 g) and the resultant mixture heated to 110° C. After $CO_2$ evolution ceased, the reaction mixture was heated for an additional 2 hours at 110° C. The dimethylformamide was stripped and the resultant solid taken up in benzene and petroleum ether. The resulting slurry was allowed to cool, chilled and the title compound was obtained as a yellow solid following filtration and drying (61.5 percent yield), m.p. 122°–123° C.

Analysis—calculated for $C_{19}H_{13}Cl_2N_2O_2$(%): C, 59.1; H, 3.4; N, 10.9. Found (%): C, 58.5; H, 3.8; N, 10.2.

EXAMPLE 8

4-Phenylsulfonyl-5,6-Bisphenyl-2H-Pyridazin-3-One

Benzilmonohydrazone (20.3 g) and ethyl α-phenylsulfonylacetate (22.8 g) were charged to a dry reaction flask in absolute ethanol (250 ml). With stirring, sodium ethoxide (6.8 g) was added portionwise When addition was complete, the reaction was heated to reflux for 12 hours. During this time, a 10 percent excess (2.3 g) of the ester was added. The cooled solution was quenched in an equal volume of water and concentrated HCl was added to precipitate a solid. The product was filtered from the cold mixture and recrystallized from ethanol to obtain the title compound as a white solid (34 percent yield), m.p. 254°–256° C.

Analysis—calculated for $C_{22}H_{16}N_2O_3S$ (%): C, 68.02; H, 4.15% N, 7.21 Found (%): C, 68.52; H, 4.23; N, 7.21. Found (%): C, 68.52; H, 4.23; N, 7.88.

EXAMPLE 9

1-[4'-Acetyl-5',6'-Bis(p-Chlorophenyl)-2H-Pyridazin-3'-One-2'-yl]Acetamide

4-Acetyl-5,6-bis(p-chlorophenyl)-2H-pyridazin-3-one (35.0 g) and potassium carbonate (14.0 g) were slurried in dimethylformamide (500 ml) and chloroacetamide (11.0 g) was added dropwise in dimethylforoamide. After the addition was complete, the reaction mixture was heated at 95° C. for 5 hours. The reaction mixture was allowed to cool to room temperature and water (400 ml) was added to the reaction mixture. The resulting solution was filtered aadn an additional 100 ml of water added. Upon standing, a solid precipitated which was recovered and allowed to dry overnight to obtain the title compound (87 percent yield), m.p. 228°–230° C.

Analysis—calculated for $C_{20}H_{15}Cl_2N_3O_3$ (%): C, 57.71; H, 3.63; N 10.09. Found (%): C, 57.92; H, 3.67; N-10.26.

EXAMPLE 10

Ethyl-4-[4'-Acetyl-5',6'-Bis(p-Chlorophenyl)Pyridazin-3'-One-2'-yl]Butyrate

4-Acetyl-5,6-bis(p-chlorophenyl)-2H-pyridazin-3-one (15.0 g) and potassium carbonate (6.4 g) were charged to a reaction flask in dimethylformamide (200 ml). With stirring, the reaction mixture was heated to 80° C., at which point ethyl-4-bromobutyrate (8.9 g) was added dropwise to the reaction mixture. The mixture was heated for about 7 hours and cooled to room temperature and diluted with 3 volumes of water. The resulting precipitate was separated, washed with water and recrystallized after air drying to yield the title compound as an off-white solid (55.3 percent yield), m.p. 100°–103° C.

Analysis—calculated for $C_{24}H_{22}Cl_2N_2O_4$ (%): C, 60.89; H, 4.68; N, 5.91. Found (%): C, 61.25; H, 4.70; N, 5.91.

EXAMPLE 11

2-(2'-Dimethylaminoethyl)-4-Acetyl-5,6-Bis(p-Chlorophenyl)-2H-Pyridazin-3-One

4-Acetyl-5,6-bis(p-chlorophenyl)-2H-pyridazin-3-one (20.0 g), potassium carbonate (9.0 g) and 30 ml of a toluene solution of N-(2-chloroethyl)dimethylamine (0.34 g/ml) and dimethylformamide (150 ml) were stirred at 80° C. for 18 hours. A second equivalent of the amine was added and heating continued for an additional four hours. The mixture was cooled, poured into water and the suspension extracted with ethyl acetate. The combined organic extracts were dried and evaporated in vacuo. Following purification by dry column silica gel chromatography and recrystallization, the title compound was obtained (63 percent yield), m.p. 149°–150° C.

Analysis—calculated for $C_{22}H_{21}Cl_2N_3O_2$ (%): C, 61.04; H, 4.92; N, 9.76. Found (%): C, 61.21; H, 4.95; N, 10.07.

EXAMPLE 12

Potassium 2-[4'-Acetyl-5',6'-Bis(p-Chlorophenyl) Pyridazin-3-One-2'-yl]Ethyl Hemisuccinate Monohydrate To a solution of 2-[4'-acetyl-5',6'-bis(p-chlorophenyl)-pyridazin-3-one-2'-yl]ethyl hemisuccinate (5.5 g) in t-butanol (60 ml) under dry nitrogen was added potassium t-butoxide (1.23 g) in t-butanol. The resulting precipitate was separated by filtration and washed with butanol and ethyl ether to yield the title compound (39 percent yield), m.p. 145°–150° C. (dec.).

Analysis—calculated for $C_{24}H_{19}Cl_2KN_2O_6$(%): C, 51.52; H, 3.78; N, 5.01. Found (%): C, 51.88; H, 3.98; N, 4.85.

The following compounds were prepared utilizing synthesis methods analogous to the foregoing.

EXAMPLE 13

2-(2'-hydroxyethyl)-4-acetyl-5,6-diphenyl-2H-pyridazin-3-one, m.p. 126°–128° C.

EXAMPLE 14

2-methylthiomethyl-4-acetyl-5,6-diphenyl-2H-pyridazin-3-one, m.p. 119°–122° C.

EXAMPLE 15

2-[4'-cyano-5',6'-bis(p-chlorophenyl)pyridazin-3-one-2'-yl]ethyl hemisuccinate, m.p. 157°–158° C.

EXAMPLE 16

2-(4',5',6'-triphenyl-pyridazin-3'-one-2'-yl) ethyl hemisuccinate, m.p. 180°–181° C.

EXAMPLE 17

4-[4'-cyano-5',6'-bis(p-chlorophenyl)pyridazin-3'-one-2'-yl]butyric acid, m.p. 163°–165° C.

EXAMPLE 18

2-(2'-hydroxyethyl)-4-(p-chlorophenyl)-5,6-diphenyl-2H-pyridazin-3-one, m.p. 183°–185° C.

EXAMPLE 19

2-(2'-hydroxyethyl)-4-naphthyl-5,6-bisphenyl-2H-pyridazin-3-one, m.p. 197°–199° C.

EXAMPLE 20

2-(2'-hydroxyethyl)-4-(2',5'-dimethoxyphenyl)-5,6-diphenyl-2H-pyridazin-3-one, m.p. 211°–214° C.

EXAMPLE 21

2-(2'-hydroxyethyl)-4-(3',4'-dimethoxyphenyl)-5,6-bis(p-methoxyphenyl)-2H-pyridazin-3-one, m.p. 164°–167° C.

EXAMPLE 22

2-hydroxyisopropyl-4-acetyl-5,6-bis(p-chlorophenyl)-2H-pyridazin-3-one, m.p. 190°–192° C.

EXAMPLE 23

2-(2'-hydroxyethyl)-4-(4'-dimethylaminophenyl)-5,6-bis(p-chlorophenyl)-2H-pyridazin-3-one, m.p. 154°–157° C. (dec.)

EXAMPLE 24

4-acetylhydrazono-5,6-diphenyl-2H-pyridazin-3-one, m.p. 264°–266° C. (dec.)

EXAMPLE 25

2-[4'-acetyl-5',6'-bis(p-chlorophenyl)-pyridazin-3'-one-2'-yl]ethyl acetate, m.p. 99°–102° C.

EXAMPLE 26

2-(2'-hydroxyethyl)-4-phenyl-5,6-bis(p-chlorophenyl)-2H-pyridazin-3-one(hemihydrate), m.p. 179°–180° C.

EXAMPLE 27

2-[2'-(1-morpholinyl)ethyl]-4-acetyl-5,6-bis(p-chlorophenyl)-2H-pyridazin-3-one, m.p. 194°–198° C.

EXAMPLE 28

2-(2'-aminoethyl)-4-acetyl-5,6-bis(p-chlorophenyl)-2H-pyridazin-3-one(hydrobromide), m.p. 160°–162° C. (dec.)

EXAMPLE 29

2-[4'-acetyl-5',6'-bis(p-chlorophenyl)-pyridazin-3'-one-2'-yl]ethyl pivalate, m.p. 45°–49° C.

EXAMPLE 30

2-[2'-(1-piperidinyl)ethyl]-4-acetyl-5,6-bis(p-chlorophenyl)-2H-pyridazin-3-one, m.p. 155°–157° C.

EXAMPLE 31

2-[2'-(dimethylamino)ethyl]-4-acetyl-5,6-bis(p-chlorophenyl)-2H-pyridazin-3-one, m.p. 253°–255° C.

EXAMPLE 32

2-[4'-acetyl-5',6'-bis(p-chlorophenyl)-pyridazin-3'-one-2'-yl]ethyl propionate, m.p. 82°–86° C.

EXAMPLE 33

2-[2'-(1-pyrrolidinyl)ethyl]-4-acetyl-5,6-bis(p-chlorophenyl)-2H-pyridazin-3-one, m.p. 184°–186° C.

EXAMPLE 34

2-[2'-(isopropylideneamino)ethyl]-4-acetyl-5,6-bis(p-chlorophenyl)-2H-pyridazin-3-one, m.p. 191°–193° C.

EXAMPLE 35

2-[4'-acetyl-5',6'-bis(p-chlorophenyl)-pyridazin-3'-one-2'-yl]ethyl formate, m.p. 99°–100° C.

EXAMPLE 36

2-[4'-acetyl-5',6'-bis(p-chlorophenyl)-pyridazin-3'-one-2'-yl]ethyl isobutyrate (amorphous).

EXAMPLE 37

2-[4'-acetyl-5',6'-bis(p-chlorophenyl)-pyridazin-3'-one-2'-yl]ethyl octadecanoate, m.p. 43°–46° C.

EXAMPLE 38

2-[4'-acetyl-5',6'-bis(p-chlorophenyl)-pyridazin-3'-one-2'-yl]ethyl benzoate, m.p. 98°–100° C.

EXAMPLE 39

2-[4'-acetyl-5=,6'-bis(p-chlorophenyl)-pyridazin-3'-one-2'-yl]ethyl phenylacetate, m.p. 134°–135° C.

EXAMPLE 40

2-(2'-acetamidoethyl)-4-acetyl-5,6-bis(p-chlorophenyl)2H-pyridazin-3-one, m.p. 154°–157° C.

EXAMPLE 41

2(2'-methoxyethyl)-4-acetyl-5,6-bis(p-chlorophenyl)-2H-pyridazin-3-one, m.p. 127°–128° C.

EXAMPLE 42

4-acetyl-5,6-bis(p-fluorophenyl)-2H-pyridazin-3-one, m.p. 278°–281° C.

EXAMPLE 43

2-(2'-hydroxyethyl)-4-acetyl-5,6-bis(p-fluorophenyl)-2H-pyridazin-3-one, m.p. 171°–174° C.

EXAMPLE 44

2-[2'-(isopropylamino)ethyl]-4-acetyl-5,6-bis(p-chlorophenyl)-2H-pyridazin-3-one, m.p. 135°–138° C.

EXAMPLE 45

2-[2'-(4'-carbethoxypiperazinyl)ethyl]-4-acetyl-5,6-bis(p-chlorophenyl)-2H-pyridazin-3-one, m.p. 129°–131° C.

The following examples further illustrate the preparation of benzyloxycarbonyl, or the equivalent, t-butyloxycarbonyl, N-protected and deprotected amino acid ester derivatives of the present invention.

EXAMPLE 47

2-[4'-Acetyl-5',6'-Bis(p-Chlorophenyl)-Pyridazin-3'-One-2'-yl]Ethyl Glycinate (Hydrobromide) Monohydrate N-carbobenzyloxy (CBZ)-glycine (10.0 g) and 200 ml of freshly distilled pyridine were cooled in an ice bath under an argon atmosphere. To this cooled solution was added dicyclohexyl-carbodiimide (10.0 g) in 25 ml of freshly distilled pyridine. 2-(2'-Hydroxyethyl)-4-acetyl-5,6-bis(p-chlorophenyl)-2H-pyridazin-3-one (20.0 g) in 100 ml of freshly distilled pyridine was added dropwise. Upon completion of the addition, the ice bath was removed and the solution allowed to stir at 20° C. for 4 hours. An additional 1.0 g of CBZ-glycine and 1.0 g of dicyclohexyl-carbodiimide were added and the mixture stirred for an additional 2 hours. The mixture was filtered and the residue and flask washed with xylene. The filtrate was refrigerated for 18 hours. The filtrate was then refiltered and concentrated under reduced pressure. The residual light green oil was slurried in diethyl ether and allowed to stand at 20° C. for 3 hours. The suspension was filtered and the diethyl ether removed. The residual oil was chromatographed on a dry silica gel column (1 m×70 mm flat diameter) using 50/50 ethyl acetate/chloroform as the eluent. The UV absorbing (R$_f$=0.65) portion of the column was extracted with acetonitrile and the extract stored for 18 hours in the refrigerator. The solvent was removed and the flask evacuated for 4 hours at 20° C.

20.0 g of the material thus obtained was dissolved in 75 ml of glacial acetic acid and 75 ml of 4 N HBr/acetic acid was added. The flask was stored in the dark for 1 hour at 20°–22° C. The solution was then diluted to 900 ml with anhydrous ether and placed in the refrigerator. After 1 hour, the milky suspension was decanted and the residual oil washed with diethyl ether (2×200 ml). The residue was dissolved in water, frozen and lyophilized to produce the title compound as a fluffy, off-white solid (37 percent yield) which softens at 110° C.

Analysis—calculated for $C_{22}H_{19}Cl_2N_3O_4.H_2O$ HBr(%):C, 47.24; H, 397; N,7.51. Found (%):C,47.18; H,3.93; N,7.56.

EXAMPLE 48

2-[4'-Acetyl-5',6'-Bis(p-Chlorophenyl)-Pyridazin-3'-One-2'-yl]Ethyl Glycinate (Hemitartrate)

The compound of Example 47 (10.0 g) was partitioned between diethyl ether and 1 N sodium hydroxide. The diethyl ether was dried (sodium carbonate) and filtered. To one-half of the diethyl ether solution was added one equivalent of D-tartaric acid in tetrahydrofuran. The resulting precipitate was washed with diethyl ether and dried to yield the title compound (45 percent yield); which softens at 100° C.

Analysis—calculated for $C_{22}H_{19}Cl_2N_3O_4.(C_4H_6O_6)$ (%): C, 51.16; H, 4.13; N,6.88. Found (%): C, 50.92; H, 4.19; N, 6.67.

EXAMPLE 49

2-[4'-Acetyl-5',6'-Bis(p-Chlorophenyl)-Pyridazin-3'-One-2'-yl]Ethyl N-benzyloxycarbonyl Phenylalaninate To a stirred ice-cold solution of N-benzyloxycarbonyl-L-phenylalanine (14.97 g) in 100 ml of freshly distilled pyridine was added, at one time, dicyclohexyl carbodiimide (11.35 g) in 50 ml of freshly distilled pyridine. An argon atmosphere was maintained throughout the reaction. Immediately after the dicyclohexyl-carbodiimide addition, a dropwise addition of 2-(2'-hydroxyethyl)-4-acetyl-5,6-bis(p-chlorophenyl)-2H-pyridazin-3-one (20.0 g) in 200 ml of freshly distilled pyridine was started. After completion of this addition, the ice bath was removed and the solution stirred at room temperature for 88 hours. The reaction mixture was filtered and the precipitate washed with xylene followed by concentration of the filtrate. The resulting residue was chromatographed using a dry silica gel column and 90/10 chloroform/ethyl acetate as the elutent to remove dicyclohexyl carbodiimide (or dicyclohexylurea). After drying for 68 hours, the title compound was obtained as a yellow crystalline powder (41.7 percent yield), m.p. 59°–60° C.

Analysis—calculated for $C_{37}H_{31}Cl_2N_3O_6$(%): C,64.92; H, 4.49; N, 6.14. Found (%): C, 65.3; H, 4.5; N, 6.6.

The following additional compounds were similarly prepared using the foregoing synthesis methods with appropriate selection of the N-protected amino acid reactant and/or cleavage of the N-protecting group.

EXAMPLE 50

2-[4'-acetyl-5',6'-bis(p-chlorophenyl)-pyridazin-3'-one-2'-yl]ethyl lysinate (dihydrobromide), softens at 125° C.

EXAMPLE 51

2-[4'-acetyl-5=,6'-bis(p-chlorophenyl)-pyridazin-3'-one-2'-yl]ethyl glycinate (hydrochloride hemihydrate), m.p. 127°–130° C.

EXAMPLE 52

2-[4'-acetyl-5',6'-bis(p-chlorophenyl)-pyridazin-3'-one-2'-yl]ethyl ($N^1$-benzyloxycarbonyl-$N^4$-nitro) argininate, m.p. 85°–87° C.

EXAMPLE 53

2-[4'-acetyl-5',6'-bis(p-chlorophenyl)-pyridazin-3'-one-2'-yl]ethyl (N-benzyloxycarbonyl)-$\beta$-alaninate, m.p. 49°–52° C.

EXAMPLE 54

2-[4'-acetyl-5',6'-bis(p-chlorophenyl)-pyridazin-3'-one-2'-yl]ethyl (N-benzyloxycarbonyl)valinate, m.p. 112°–113° C.

EXAMPLE 55

2-[4'-acetyl-5',6'-bis(p-chlorophenyl)-pyridazin-3'-one-2'-yl]ethyl lysinate (dihydrochloride hydrate), m.p. 140°–144° C. (dec.)

EXAMPLE 56

2-[4'-acetyl-5',6'-bis(p-chlorophenyl)-pyridazin-3'-one-2'-yl]ethyl phenylalaninate (hydrochloride hydrate), m.p. 123°–126° C.

EXAMPLE 57

2-[4'-acetyl-5',6'-bis(p-chlorophenyl)-pyridazin-3'-one-2'-yl]ethyl valinate (hydrochloride hydrate), m.p. 124°–128° C.

EXAMPLE 58

2-[4'-acetyl-5',6'-bis(p-chlorophenyl)-pyridazin-3'-one-2'-yl]ethyl alaninate (hydrochloride hemihydrate), m.p. 138°–140° C.

EXAMPLE 59

2-[4'-acetyl-5',6'-bis(p-chlorophenyl)-pyridazin-3'-one-2'-yl]ethyl methioninate (hydrochloride hydrate), m.p. 102°–105° C.

The following further examples illustrate the preparation of carbohydrate derivatives of the present invention.

EXAMPLE 60

2-(2-$\beta$-D-Glucopyranosylethyl)-4-Acetyl-5,6-Bis(4-Chlorophenyl)-2H-Pyridazin-3-One A mixture of 1-O-(2-bromoethyl)-2,3,4,6-tetra-O-acetyl-$\alpha$-D-glucopyranoside (4.6 g), 2-(2-hydroxyethyl)-4-acetyl-5,6-bis(p-chlorophenyl)-2H-pyridazin-3-one (3.6 g), potassium carbonate (2.8 g) and dimethyl formamide (30 ml) was stirred at 75° C. for 2 hours. Thin layer chromatography (silica gel, $C_6H_6$/EtOAc:6/4) showed none of the starting materials and a major spot which ran close to the starting pyridazinone. The mixture was cooled and poured into $H_2O$ (300 ml) with stirring. The tan solid which separated was collected by filtration, washed with water and air dried. The moist solid was dissolved in chloroform and the solution dried ($CaSO_4$). The solvent was evaporated in vacuo to give a tan foam (7.4 g) which was chromatographed on a dry column of silica gel and eluted with diethylether. Fractions containing the product were eluted from the adsorbent with anhydrous acetone. The acetone solution was dried ($CaSO_4$) and evaporated in vacuo to a tan foam (6.0 g).

To a stirred solution of the thus obtained protected glucoside (6.0 g) and absolute methanol (50 ml) was added potassium carbonate (0.20 g). The resulting mixture was stirred at 20° C. for 1 hour. Thin layer chromatography (silica gel, $C_6H_6$/EtOAc:6/4) showed no starting material and only a spot at the origin. Thin layer chromatography (silica gel, EtOAc/MeOH:8/2 or acetone) showed only one spot. The mixture was adjusted to ca pH 6 with Biorad AG 50W-X12 ion exchange resin (H+ form) (styrene sulfonic acid resin) and then evaporated in vacuo to a yellow foam (4.5 g). On standing at 20° C., the foam changed to a heavy, thick syrup which partially crystallized. This product was dissolved in benzene, treated with charcoal at 80° C. and the mixture was filtered. The benzene filtrate was frozen in a dry ice/isopropanol bath, and the resulting solid lyophilized to yield the title compound as a white, fluffy solid (37 percent yield), m.p. 96°–122° C.

Analysis—calculated for $C_{26}H_{26}Cl_2N_2O_8$ (%): C, 55.23; H, 4.64; N, 4.95. Found (%): C, 55.04; H, 4.74; N, 4.96.

EXAMPLE 61

1-O-[2-(4-Acetyl-5,6-Bis(4-Chlorophenyl)-2H-Pyridazin-3-One-2-yl]Ethyl-$\beta$-D-Glucuronic Acid To a stirred solution of NaOH (0.2 g) and anhydrous methanol (500 ml) was added D-glucurono-3,6-lactone (88.0 g) portionwise during 0.5 hours. The resulting mixture was stirred at 20° C. for 1.5 hours, filtered and evaporated in vacuo (30° C.). The resulting methyl glucuronate (114 g) was used without further purification.

To a stirred (−15° C.) solution of crude methyl glucuronate (114 g) and anhydrous pyridine (200 ml) was added acetic anhydride (200 ml) dropwise during 2.25 hours. The cooling bath was removed, the dark brown solution stirred at 20° C. for 1 hour and evaporated in vacuo. The dark brown syrup was dissolved in chloroform (300 ml) and the solution was washed with $H_2O$ (1×500 ml), 1 N HCl (2×500 ml), $H_2O$ (1×500 ml), saturated sodium bicarbonate (3×500 ml), $H_2O$ (1×500 ml), dried ($CaSO_4$) and evaporated in vacuo. The resulting brown syrup was triturated with 95 percent ethanol (100 ml). The solid which separated was collected by filtration, washed with 95 percent ethanol and air dried. The solid (32.6 g) was a mixture of the $\alpha$ and $\beta$ methyl 1,2,3,4-tetra-O-acetyl-D-glucuronates. [The combined filtrate and washings were evaporated in vacuo to a brown syrup (74.0 g) which was also mainly the desired product.] Thin layer chromatography system: toluene/EtOAc:8/2—[m.p.—($\alpha$) 111°–112° C.; m.p. ($\beta$) 172°–175° C.]

A mixture of methyl 1,2,3,4-tetra-O-acetyl-$\alpha$($\beta$)-D-glucuronate (32.6 g) and 30 percent HBr in glacial acetic acid was submerged in an oil bath (70° C.) and the mixture stirred for 1 hour, cooled and evaporated in vacuo. The residue was dissolved in chloroform (100 ml), and the solution was washed with $H_2O$ (1×100 ml), 5 percent sodium bicarbonate (2×100 ml), $H_2O$ (1×100 ml), dried ($CaSO_4$) and evaporated in vacuo to a red syrup (24.2 g). The crude methyl 2,3,4-tri-O-acetyl-1-bromo-1-deoxy-$\alpha$-D-glucuronate was used without further purification (thin layer chromatography system: toluene/EtOAc:6/4). (The bromo compound can be chromatographed on a dry silica gel column and eluted with diethylether/petroleum ether:4/1; m.p. 82°–84° C.)

A stirred mixture of crude methyl 2,3,4-tri-O-acetyl-1-bromo-1-deoxy-α-D-glucuronate (3.19 g), 2-chloroethanol (96.6 g), anhydrous toluene (100 ml) and silver carbonate (33.1 g) was submerged in an oil bath (50° C.) for 1 hour. The suspension was filtered, and the residue washed with toluene. The combined filtrate was washed with $H_2O$ (2×200 ml), dried ($CaSO_4$) and evaporated in vacuo. The orange crystalline residue was triturated with 95 percent ethanol, collected by filtration, washed with 95 percent ethanol and air-dried (13.2 g). The methyl 2,3,4-tri-O-acetyl-1-O-(2-chloroethyl)-β-D-glucuronate was used without further purification (thin layer chromatography system: $CHCl_3$). [The chloro compound can be recrystallized from 95 percent ethanol; m.p. 138°–139° C.]

A solution of crude methyl 2,3,4-tri-O-acetyl-1-O-(2-chloroethyl)-β-D-glucuronate (13.2 g), sodium iodide (4.95 g) and methyl ethyl ketone (50 ml) was stirred under reflux for 6 hours. The resulting mixture was cooled, filtered and the residue washed with anhydrous acetone. The combined filtrate and washings were evaporated in vacuo to a tan crystalline solid (16.1 g). The crude methyl 2,3,4-tri-O-acetyl-1-O-(2-iodoethyl)-β-D-glucuronate was used without further purification (thin layer chromatography system: toluene/EtOAc:6/4).

The crude methyl 2,3,4-tri-O-acetyl-1-O-(2-iodoethyl)-β-D-glucuronate (16.1 g), 4-acetyl-5,6-bis(p-chlorophenyl)-2-(2-hydroxyethyl)-2H-pyridazin-3-one (11.8 g), potassium carbonate (9.1 g) and dimethyl formamide (50 ml) were stirred at 20° C. for 17 hours. The brown mixture was evaporated in vacuo, and the residue was triturated with $H_2O$ (100 ml). The mixture was filtered, and the insoluble brown solid was washed with $H_2O$. The solid was dissolved in methylene chloride, the solution dried ($CaSO_4$) and evaporated in vacuo. The resulting brown syrup was applied to a dry column of silica gel and eluted with diethylether/petroleum ether:4/1. Fractions containing product were eluted with ethyl acetate. The ethyl acetate solution was evaporated in vacuo to a yellow syrup which was triturated with anhydrous methanol. The amorphous white solid which separated was collected by filtration and air dried (8.8 g). The methyl 1-O-[2-(4-acetyl-5,6-bis(4-chlorophenyl)-3-oxopyridazin-2-yl)ethyl]-2,3,4-tri-O-acetyl-β-D-glucuronate was used without further purification (thin layer chromatography system: diethylether/petroleum ether:4/1).

To a stirred solution of methyl 1-O-[2-(4-acetyl-5,6-bis(4-chlorophenyl)-3-oxopyridazin-2-yl)ethyl]-2,3,4-tri-O-acetyl-β-D-glucuronate (3.7 g) and anhydrous methanol (25 ml) was added potassium carbonate (0.12 g). The resulting mixture was stirred at 20° C. for 1 hour. The pH of the mixture was adjusted to ca 5.5 with Biorad 50W-X-12 resin (H+) and filtered. The filtrate was evaporated in vacuo, and the resulting tan foam was applied to a dry silica gel column and eluted with chloroform/acetone:1/1. Fractions containing the product were eluted with ethyl acetate and the extract concentrated in vacuo. The resulting pale yellow foam (1.8 g) was methyl 1-O-[2-(4-acetyl-5,6-bis(4-chlorophenyl)-3-oxopyridazin-2-yl)ethyl]-β-D-glucuronate (thin layer chromatography system: chloroform/acetone:1/1).

To a stirred solution of methyl 1-O-[2-(4-acetyl-5,6-bis(4-chlorophenyl)-3-oxopyridazin-2-yl)ethyl]-β-D-glucuronate (1.8 g) and anhydrous methanol (20 ml) was added $H_2O$ (10 ml) dropwise. Anhydrous potassium carbonate (0.5 g) was added in one portion and the resulting mixture was stirred at 20° C. for 2 hours. The pH of the solution was adjusted to ca 5.5 with Biorad 50W-X-12 resin (H+) and filtered. The filtrate was evaporated in vacuo to give a yellow foam (1.8 g) which was dissolved in $H_2O$ (50 ml) and lyophilized. The resulting fluffy white solid (1.5 g) was potassium 1-O-[2-(4-acetyl-5,6-bis(4-chlorophenyl)-3-oxopyridazin-2-yl)ethyl]-β-D-glucuronate (thin layer chromatography system: n-butanol/95 percent ethanol/water:40/10/12).

The pH of a solution of potassium 1-O-[2-(4-acetyl-5,6-bis(4-chlorophenyl)-3-oxopyridazin-2-yl)ethyl]-β-D-glucuronate (1.1 g) and $H_2O$ (25 ml) was adjusted to ca 3.0. The mixture was filtered, and the resin was washed with $H_2O$. The combined milky filtrate was lyophilized to yield the title compound as a fluffy white solid (1.0 g). Elemental analyses indicated this material contained ca 6 percent of the potassium salt and 1–2 moles of $H_2O$ of hydration (thin layer chromatography system: n-butanol/95 percent ethanol/water:40/10/12).

Analysis—calculated for $C_{26}H_{24}Cl_2N_2O_9 \cdot 2H_2O$ (%): C, 50.7; H, 4.6; N, 4.6; Cl, 11.5; K, 0.0. Found (%): C, 50.3; H, 4.3; N, 4.5; Cl, 12.1; K, 0.4.

EXAMPLE 62

Antihypertensive Activity in Spontaneously Hypertensive Rats

Spontaneously hypertensive rats, 12 to 16 weeks of age, were used in the antihypertensive assay. Systolic blood pressures were determined by the tail cuff method, utilizing capacitance transducers for the detection of pressure, an aneroid manometer for measuring pressure, and an oscilloscope for visualizing the disappearance and/or appearance of the pressure pulse. Heart rate was measured by a biotachometer. Groups of five rats having systolic blood pressures of 170 mmHg or greater where chosen and the test compounds administered at the doses indicated below (oral) as a solution or suspension in 0.25 percent methylcellulose (MC) at a volume of 5 ml/kg. One group served as the control and received the vehicle. Four and twenty-four hours after dosing, systolic blood pressure and heart rate were recorded. A second dose of compound was administered and blood pressure and heart rate determined at 4 and 24 hours after the second dose.

The results observed with respect to preferred compounds are set forth in Table I below:

TABLE I

| Compound Example No. | Dose (mg/kg) | SHR Assay Mean Systolic Blood Pressure (mm/Hg) | | | | | Heart Rate (change) |
|---|---|---|---|---|---|---|---|
| | | Pre-dose | Postdose 1 | | Postdose 2 | | |
| | | | 4 hr. | 24 hr. | 4 hr. | 24 hr. | |
| 2 | 100 | 218 | 173 | 185 | 174 | 192 | + |
| 5 | 25 | 190 | 181 | 184 | 182 | 185 | 0 |
|   | 50 | 195 | 182 | 186 | 180 | 188 | + |
| 7 | 10 | 194 | 181 | 183 | 178 | 180 | 0 |
|   | 100 | 203 | 176 | 167 | 158 | 171 | 0 |
| 8 | 100 | 190 | 185 | 171 | 183 | 192 | 0 |
| 10 | 100 | 196 | 192 | 174 | 188 | 181 | 0 |
| 11 | 100 | 201 | 182 | 179 | 155 | 144 | 0 |
| 12 | 10 | 196 | 168 | 196 | 187 | 187 | 0 |
| 13 | 50 | 220 | 217 | 206 | 220 | 221 | + |
|   | 75 | 200 | 181 | 163 | 164 | 176 | 0 |

TABLE I-continued
SHR Assay
Mean Systolic Blood Pressure (mm/Hg)

| Compound Example No. | Dose (mg/kg) | Pre-dose | Postdose 1 4 hr. | Postdose 1 24 hr. | Postdose 2 4 hr. | Postdose 2 24 hr. | Heart Rate (change) |
|---|---|---|---|---|---|---|---|
| 14 | 100 | 197 | 187 | 192 | 183 | 191 | 0 |
| 15 | 100 | 208 | 171 | 169 | 142 | 162 | 0 |
| 16 | 100 | 195 | 176 | 186 | 176 | 187 | 0 |
| 17 | 100 | 215 | 202 | 204 | 175 | 180 | 0 |
| 18 | 100 | 212 | 190 | 207 | 195 | 205 | 0 |
| 19 | 100 | 198 | 188 | 182 | 177 | 183 | 0 |
| 20 | 100 | 196 | 170 | 184 | 183 | 188 | 0 |
| 21 | 100 | 196 | 184 | 178 | 185 | 195 | 0 |
| 22 | 100 | 212 | 186 | 174 | 191 | 201 | 0 |
| 23 | 100 | 223 | 184 | 199 | 188 | 208 | 0 |
| 24 | 100 | 206 | 207 | 181 | 179 | 192 | 0 |
| 25 | 10 | 183 | 162 | 181 | 149 | 176 | 0 |
| 26 | 100 | 195 | 185 | 194 | 179 | 170 | 0 |
| 27 | 100 | 201 | 140 | 161 | 146 | 177 | 0 |
| 28 | 25 | 194 | 184 | 162 | 177 | 183 | 0 |
| 29 | 10 | 190 | 172 | 185 | 180 | 191 | 0 |
|  | 30 | 205 | 200 | 202 | 158 | 205 | — |
| 30 | 100 | 192 | 180 | 163 | 165 | 176 | 0 |
| 31 | 100 | 205 | 200 | 170 | 160 | 184 | + |
| 32 | 3 | 190 | 173 | 185 | 188 | 188 | 0 |
|  | 30 | 181 | 133 | 136 | 129 | 168 | + |
| 33 | 30 | 212 | 200 | 187 | 191 | 199 | 0 |
| 34 | 30 | 211 | 201 | 196 | 190 | 198 | 0 |
| 35 | 30 | 174 | 129 | 138 | 112 | 155 | + |
| 36 | 30 | 201 | 195 | 201 | 182 | 190 | 0 |
| 37 | 30 | 181 | 168 | 162 | 142 | 137 | 0 |
| 38 | 30 | 173 | 116 | 139 | 136 | 130 | 0 |
| 39 | 30 | 174 | 165 | 154 | 146 | 127 | 0 |
| 40 | 100 | 220 | 149 | 146 | 136 | 145 | — |
| 41 | 100 | 232 | 205 | 195 | 216 | 223 | — |
| 42 | 100 | 186 | 138 | 160 | 166 | 180 | 0 |
| 43 | 100 | 186 | 142 | 148 | 144 | 158 | 0 |
| 44 | 100 | 216 | 211 | 181 | 143 | 176 | 0 |
| 45 | 100 | 200 | 186 | 182 | 151 | 183 | 0 |
| 47 | 10 | 182 | 177 | 154 | 145 | 170 | 0 |
| 48 | 10 | 200 | 179 | 178 | 165 | 175 | 0 |
| 49 | 100 | 184 | 145 | 184 | 144 | 182 | 0 |
| 50 | 50 | 231 | 179 | 173 | —[1] | — | + |
| 51 | 3 | 205 | 202 | 194 | 193 | 198 | 0 |
| 52 | 100 | 178 | 133 | 136 | 128 | 143 | 0 |
| 53 | 100 | 196 | 178 | 188 | —[1] | — | 0 |
| 54 | 100 | 192 | 202 | 202 | —[1] | — | + |
| 55 | 15.4[2] | 181 | 169 | 171 | 166 | 185 | 0 |
| 56 | 10 | 200 | 188 | 197 | 185 | 199 | 0 |
| 57 | 10 | 204 | 191 | 196 | 179 | 200 | + |
| 58 | 10 | 215 | 210 | 215 | 195 | 209 | 0 |
| 59 | 10 | 191 | 176 | 193 | 173 | 194 | 0 |
| 60 | 10 | 192 | 200 | 173 | 166 | 178 | 0 |
| 61[3] | 30 | 202 | 170 | 184 | 179 | 188 | 0 |
|  | 100 | 200 | 153 | 158 | 150 | 174 |  |

[1] no second dose given
[2] administered subcutaneously
[3] blood pressure readings are for a single dose at 4, 24, 28 and 48 hours, respectively.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the mammal treated, severity of hypertension, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A compound of the formula

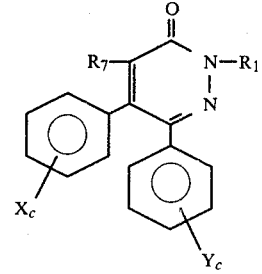

or a pharmaceutically acceptable nontoxic salt thereof wherein $R_1$ is hydrogen, $C_1$-$C_4$ hydroxyalkyl, carbonyl($C_1$-$C_4$)alkyl, $C_1$-$C_6$ carboxyalkyl, $C_1$-$C_6$ alkoxycarbonyl($C_1$-$C_6$)alkyl, $C_1$-$C_6$ alkoxy($C_1$-$C_6$)alkyl; or the group

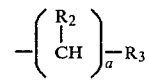

where a is 1 to 4, inclusive, $R_2$ is hydrogen or $C_1$-$C_4$ alkyl and $R_3$ is amino, methylthio, $C_1$-$C_6$ alkylamino, $C_1$-$C_6$ alkylimino, $C_1$-$C_6$ alkanoylamino, $C_1$-$C_6$ alkoxycarbonyl amino, morpholinyl, piperizinyl, ($C_1$-$C_6$ alkoxycarbonyl)-piperizinyl, piperidinyl, pyrrolidinyl, glucuronyl or glucopyranosyl; or the group

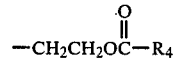

where $R_4$ is hydrogen, $C_1$-$C_{20}$ alkyl, $C_1$-$C_6$ carboxyalkyl, phenyl, phenyl($C_1$-$C_6$)alkyl or $R_4$ represents the group

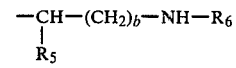

where b is 0 to 4, inclusive, $R_5$ is hydrogen, $C_1$-$C_4$ alkyl, methylthioethyl, benzyl, $NH_2$, or benzyloxycarbamyl, and $R_6$ is hydrogen, benzyloxycarbonyl, t-butyloxycarbonyl or

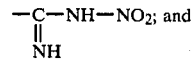

$R_7$ is acetyl, cyano, phenylsulfonyl, ($C_1$-$C_4$)alkylhydrazono, naphthyl, phenyl or phenyl substituted with at least one substituent selected from the group consisting of halogen, $C_1$-$C_6$ alkylamino and $C_1$-$C_4$ alkoxy; and $X_c$ and $Y_c$ are the same or different and independently selected from the group consisting of halogen, $C_1$-$C_4$ alkyl and $C_1$-$C_4$ alkoxy where c is 0, 1 or 2;

subject to the provisos that when $R_7$ is acetyl, phenyl or cyano, $R_1$ is other than hydrogen; and when $R_7$ is cyano, $R_1$ is $C_1-C_4$ hydroxyalkyl, $C_1-C_6$ carboxyalkyl or the group

where $R_4$ is $C_1-C_6$ carboxyalkyl and $X_c$ and $Y_c$ are halo, with c being at least 1;
and the enol tautomeric derivatives thereof.

2. The compound as defined in claim 1 wherein $R_1$ is $C_1-C_4$ hydroxyalkyl, carbonyl($C_1-C_4$)alkyl, $C_1-C_6$ alkoxy ($C_1-C_6$)alkyl, morpholinyl($C_1-C_6$)alkyl, or the group

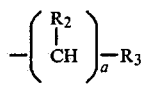

where a is 1 to 4, inclusive, $R_2$ is hydrogen and $R_3$ is amino or $C_1-C_6$ alkylamino, or the group

where $R_4$ is $C_1-C_{20}$ alkyl, $C_1-C_6$ carboxyalkyl, phenyl($C_1-C_6$)alkyl or $R_4$ represents the group

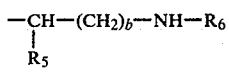

where b is 0 to 4, inclusive, $R_5$ is hydrogen, $C_1-C_4$ alkyl, methylthioethyl, benzyl, $HN_2$ or benzyloxycarbamyl, and $R_6$ is hydrogen, benzyloxycarbonyl, t-butyloxycarbonyl or

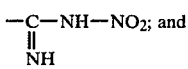

$R_7$ is acetyl, cyano, phenyl or phenyl substituted with at least one substituent selected from the group consisting of halogen, $C_1-C_6$ alkylamino and $C_1-C_4$ alkoxy; and
$X_c$ and $Y_c$ are simultaneously halogen where c is 1.

3. The compound as defined in claim 2 wherein said compound is selected from the group consisting of 2-(2'-hydroxyethyl)-4-acetyl-5,6-bis(p-chlorophenyl)-2H-pyridazin-3-one, 2-(2'-hydroxyethyl)-4,5,6-triphenyl-2H-pyridazin-3-one, 2-(2'-hydroxyethyl)-4-cyano-5,6-bis(p-chlorophenyl)-2H-pyridazin-3-one, 2-(2'-dimethylaminoethyl)-4-acetyl-5,6-bis(p-chlorophenyl)-2H-pyridazin-3-one, 2-[4'-cyano-5',6'-bis(p-chlorophenyl)-pyridazin-3'-one-2'-yl]ethyl hemisuccinate, 2-[2'-(1-morpholinyl)ethyl]-4-acetyl-5,6-bis(p-chlorophenyl)-2H-pyridazin-3-one, 2-[4'-acetyl-5',6'-bis(p-chlorophenyl)-pyridazin-3'-one-2'-yl]ethyl propionate, 2-[4'-acetyl-5',6'-bis(p-chlorophenyl)-pyridazin-3'-one-2'-yl]ethyl formate, 2-[4'-acetyl-5',6'-bis(p-chlorophenyl)-pyridazin-3'-one-2'-yl]ethyl octadecanoate, 2-[4'-acetyl-5',6'-bis(p-chlorophenyl)pyridazin-3'-one-2'-yl]ethyl benzoate, 2-(2'-acetamidoethyl)-4-acetyl-5,6-bis(p-chlorophenyl)-2H-pyridazin-3-one, 2-(2'-methoxyethyl)-4-acetyl-5,6-bis(p-chlorophenyl)-2H-pyridazin-3-one, 2-(2'-hydroxyethyl)-4-acetyl-5,6-bis(p-fluorophenyl)-2H-pyridazin-3-one, 2-[4'-acetyl-5',6'-bis(p-chlorophenyl)-pyridazin-3'-one-2'-yl]ethyl glycinate hydrobromide, 2-[4'-acetyl-5',6'-bis(p-chlorophenyl)-pyridazin-3'-one-2'-yl]ethyl glycinate hemitartrate, 2-[4'-acetyl-5',6'-bis(p-chlorophenyl)-pyridazin-3'-one-2'-yl]ethyl N-benzyloxycarbonyl phenylalaninate, 2-[4'-acetyl-5',6'-bis(p-chlorophenyl)-pyridazin-3'-one-2'-yl]ethyl lysinate dihydrobromide and 2-[4'-acetyl-5',6'-bis(p-chlorophenyl)-pyridazin-3'-one-2'-yl]ethyl ($N^1$-benzyloxycarbonyl-$N^4$-nitro) argininate.

4. The compound of claim 3 wherein said compound is 2-(2'-hydroxyethyl)-4-acetyl-5,6-bis(p-chlorophenyl)-2H-pyridazin-3-one.

5. The compound of claim 3 wherein said compound is 2-(2'-hydroxyethyl)-4-cyano-5,6-bis(p-chlorophenyl)-2H-pyridazin-3-one.

6. The compound as defined in claim 3 wherein said compound is 2-[2'-(1-morpholinyl)ethyl]-4-acetyl-5,6-bis(p-chlorophenyl)-2H-pyridazin-3-one.

7. The compound as defined in claim 3 wherein said compound is 2-(2'-acetamidoethyl)-4-acetyl-5,6-bis(p-chlorophenyl)-2H-pyridazin-3-one.

8. The compound as defined in claim 3 wherein said compound is 2-[4'-acetyl-5',6'-bis(p-chlorophenyl)-pyridazin-3'-one-2'-yl]ethyl ($N^1$-benzyloxycarbonyl-$N^4$-nitro) argininate.

9. The compound as defined in claim 3 wherein said compound is 2-[4'-acetyl-5',6'-bis(p-chlorophenyl)-pyridazin-3'-one-2'-yl]ethyl acetate.

10. The compound as defined in claim 3 wherein said compound is 2-[2'-(dimethylamino)ethyl]-4-acetyl-5,6-bis(p-chlorophenyl)-2H-pyridazin-3-one.

11. The compound as defined in claim 3 wherein said compound is 2-[4'-acetyl-5',6'-bis(p-chlorophenyl)-pyridazin-3'-one-2'-yl]ethyl lysinate (dihydrochloride hydrate).

12. A method of promoting an antihypertensive effect in an warm-blooded animal in need thereof comprising administering thereto an antihypertensively sufficient amount of a compound of the formula

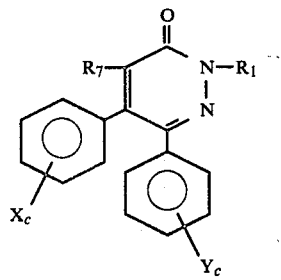

or a pharmaceutically acceptable nontoxic salt thereof wherein
$R_1$ is hydrogen, $C_1-C_4$ hydroxyalkyl, carbonyl($C_1-C_4$)alkyl, $C_1-C_6$ carboxyalkyl, $C_1-C_6$ alkoxycarbonyl($C_1-C_6$)alkyl, $C_1-C_6$ alkoxy($C_1-C_6$)alkyl; or the group

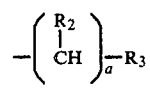

where a is 1 to 4, inclusive, $R_2$ is hydrogen or $C_1$–$C_4$ alkyl and $R_3$ is amino, methylthio, $C_1$–$C_6$ alkylamino, $C_1$–$C_6$ alkylimino, $C_1$–$C_6$ alkanoylamino, $C_1$–$C_6$ alkoxycarbonyl amino, morpholinyl, piperizinyl, ($C_1$–$C_6$ alkoxycarbonyl)-piperizinyl, piperidinyl, pyrrolidinyl, glucuronyl or glucopyranosyl; or the group

where $R_4$ is hydrogen, $C_1$–$C_{20}$ alkyl, $C_1$–$C_6$ carboxyalkyl, phenyl, phenyl($C_1$–$C_6$)alkyl or $R_4$ represents the group

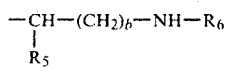

where b is 0 to 4, inclusive, $R_5$ is hydrogen, $C_1$–$C_4$ alkyl, methylthioethyl, benzyl, $NH_2$, or benzyloxycarbamyl, and $R_6$ is hydrogen, benzyloxycarbonyl, t-butyloxycarbonyl or

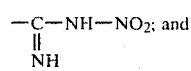

$R_7$ is acetyl, cyano, phenylsulfonyl, ($C_1$–$C_4$)alkylhydrazono, naphthyl, phenyl or phenyl substituted with at least one substituent selected from the group consisting of halogen, $C_1$–$C_6$ alkylamino and $C_1$–$C_4$ alkoxy; and $X_c$ and $Y_c$ are the same or different and independently selected from the group consisting of halogen, $C_1$–$C_4$ alkyl and $C_1$–$C_4$ alkoxy where c is 0, 1 or 2; subject to the provisos that when $R_7$ is acetyl, phenyl or cyano, $R_1$ is other than hydrogen; and when $R_7$ is cyano, $R_1$ is $C_1$–$C_4$ hydroxyalkyl, $C_1$–$C_6$ carboxyalkyl or the group

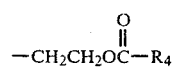

where $R_4$ is $C_1$–$C_6$ carboxyalkyl and $X_c$ and $Y_c$ are halo, with c being at least 1;

and the enol tautomeric derivatives thereof.

13. The method as defined in claim 12 wherein said compound is selected from the group consisting of 2-(2'-hydroxyethyl)-4-acetyl-5,6-bis(p-chlorophenyl)-2H-pyridazin-3-one, 2-(2'-hydroxyethyl)-4,5,6-triphenyl-2H-pyridazin-3-one, 2-(2'-hydroxyethyl)-4-cyano-5,6-bis(p-chlorophenyl)-2H-pyridazin-3-one, 2-(2'-dimethylaminoethyl)-4-acetyl-5,6-bis(p-chlorophenyl)-2H-pyridazin-3-one, 2-[4'-cyano-5',6'-bis(p-chlorophenyl)-2H-pyridazin-3'-one-2'-yl] ethyl hemisuccinate, 2-[2'-(1-morpholinyl)ethyl]-4-acetyl-5,6-bis(p-chlorophenyl)-2H-pyridazin-3-one, 2-[4'-acetyl-5',6'-bis(p-chlorophenyl)-pyridazin-3'-one-2'-yl] ethyl propionate, 2-[4'-acetyl-5',6'-bis(p-chlorophenyl)-pyridazin-3'-one-2'-yl] ethyl formate, 2-[4'-acetyl-5',6'-bis(p-chlorophenyl)-pyridazin-3'-one-2'-yl] ethyl octadecanoate, 2-[4'-acetyl-5',6'-bis(p-chlorophenyl)-pyridazin-3'-one-2'-yl] ethyl benzoate, 2-(2'-acetamidoethyl)-4-acetyl-5,6-bis(p-chlorophenyl)-2H-pyridazin-3-one, 2-(2'-methoxyethyl)-4-acetyl-5,6-bis(p-chlorophenyl)-2H-pyridazin-3-one, 2-(2'-hydroxyethyl)-4-acetyl-5,6-bis(p-fluorophenyl)-2H-pyridazin-3-one, 2-[4'-acetyl-5',6'-bis(p-chlorophenyl)-pyridazin-3'-one-2'-yl] ethyl glycinate hydrobromide, 2-[4'-acetyl-5',6'-bis(p-chlorophenyl)-pyridazin-3'-one-2'-yl] ethyl glycinate hemitartrate, 2-[4'-acetyl-5',6'-bis(p-chlorophenyl)-pyridazin-3'-one-2'-yl] ethyl N-benzyloxycarbonyl phenylalaninate, 2-[4'-acetyl-5',6'-bis(p-chlorophenyl)-pyridazin-3'-one-2'-yl] ethyl lysinate dihydrobromide and 2-[4'-acetyl-5',6'-bis(p-chlorophenyl)-pyridazin-3'-one-2'-yl] ethyl ($N^1$-benzyloxycarbonyl-$N^4$-nitro) argininate.

14. The method as defined in claim 13 wherein said compound is 2-(2'-hydroxyethyl)-4-acetyl-5,6-bis(p-chlorophenyl)-2H-pyridazin-3-one.

15. The method as defined in claim 12 wherein said antihypertensively sufficient amount ranges between about 1–300 mg/kg/day.

16. The method as defined in claim 15 wherein said antihypertensively sufficient amount ranges between about 10–150 mg/kg/day.

17. An antihypertensive composition comprised of a pharmaceutical carrier in combination with a compound of the formula

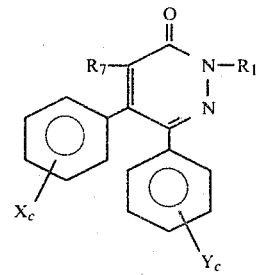

or a pharmaceutically acceptable nontoxic salt thereof wherein $R_1$ is hydrogen, $C_1$–$C_4$ hydroxyalkyl, carbonyl($C_1$–$C_4$)alkyl, $C_1$–$C_6$ carboxyalkyl, $C_1$–$C_6$ alkoxycarbonyl($C_1$–$C_6$)alkyl, $C_1$–$C_6$ alkoxy($C_1$–$C_6$)alkyl; or the group

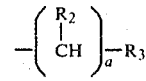

where a is 1 to 4, inclusive, $R_2$ is hydrogen or $C_1$–$C_4$ alkyl and $R_3$ is amino, methylthio, $C_1$–$C_6$ alkylamino, $C_1$–$C_6$ alkylimino, $C_1$–$C_6$ alkanoylamino, $C_1$–$C_6$ alkoxycarbonyl amino, morpholinyl, piperizinyl, ($C_1$–$C_6$ alkoxycarbonyl)-piperizinyl, piperidinyl, pyrrolidinyl, glucuronyl or glucopyranosyl; or the group

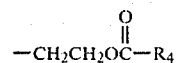

where $R_4$ is hydrogen, $C_1$–$C_{20}$ alkyl, $C_1$–$C_6$ carboxyalkyl, phenyl, phenyl($C_1$–$C_6$)alkyl or $R_4$ represents the group

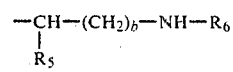

where b is 0 to 4, inclusive, $R_5$ is hydrogen, $C_1-C_4$ alkyl, methylthioethyl, benzyl, $NH_2$, or benzyloxycarbamyl, and $R_6$ is hydrogen, benzyloxycarbonyl, t-butyloxycarbonyl or

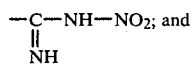

$R_7$ is acetyl, cyano, phenylsulfonyl, $(C_1-C_4)$alkylhydrazono, naphthyl, phenyl or phenyl substituted with at least one substituent selected from the group consisting of halogen, $C_1-C_6$ alkylamino and $C_1-C_4$ alkoxy; and $X_c$ and $Y_c$ are the same or different and independently selected from the group consisting of halogen, $C_1-C_4$ alkyl and $C_1-C_4$ alkoxy where c is 0, 1 or 2;

subject to the provisos that when $R_7$ is acetyl, phenyl or cyano, $R_1$ is other than hydrogen; and when $R_7$ is cyano, $R_1$ is $C_1-C_4$ hydroxyalkyl, $C_1-C_6$ carboxyalkyl or the group

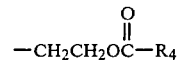

where $R_4$ is $C_1-C_6$ carboxyalkyl and $X_c$ and $Y_c$ are halo, with c being at least 1;

and the enol tautomeric derivatives thereof.

18. A method of obtaining an antihypertensive effect comprising administering the antihypertensive composition as defined in claim 17 to a warm-blooded animal in need thereof.

* * * * *

UNITED STATES PATENT AND TRADEMARK OFFICE
CERTIFICATE OF CORRECTION

PATENT NO. : 4,238,490

DATED : December 9, 1980

INVENTOR(S) : Larry J. Powers et al.

It is certified that error appears in the above-identified patent and that said Letters Patent are hereby corrected as shown below:

Column 1, line 55, after "in" insert --the--.

Column 7, line 67, "$C_{19}H_{13}Cl_2N_2O_2$" should be --$C_{19}H_{13}Cl_2N_3O_2$--.

Column 8, line 27, "dimethylforoamide" should be --dimethylformamide--;

line 32, "aadn" should be --and--; line 38, "N-" should be --N,--.

Column 11, line 7, "5=,6'" should be --5',6'--; line 64, "eluent" should be --elutent--.

Column 12, line 13, "397" should be --3.97--.

Column 13, line 2, "5=,6'" should be --5',6'--.

Column 15, line 5, "3.19" should be --31.9--.

Column 18, line 21, "carbonyl" should be --carbamyl--.

Column 19, line 14, "carbonyl" should be --carbamyl--.

Column 20, line 59, "carbonyl" should be --carbamyl--.

Column 22, line 39, "carbonyl" should be --carbamyl--.

Signed and Sealed this

Tenth Day of March 1981

[SEAL]

Attest:

Attesting Officer

RENE D. TEGTMEYER

Acting Commissioner of Patents and Trademarks